United States Patent [19]

Lewis et al.

[11] Patent Number: 5,156,847
[45] Date of Patent: Oct. 20, 1992

[54] WOUND-HEALING COMPOSITION

[75] Inventors: Walter H. Lewis, 7915 Park Dr., St. Louis, Mo. 63117; Richard J. Stonard; Beatriz Porras-Reyes, both of St. Louis, Mo.; Thomas A. Mustoe, Evanston, Ill.

[73] Assignee: Walter H. Lewis, St. Louis, Mo.

[21] Appl. No.: 585,562

[22] Filed: Sep. 20, 1990

[51] Int. Cl.⁵ .............................. A61L 15/16
[52] U.S. Cl. .................... 424/447; 424/195.1; 514/423; 514/453; 514/284
[58] Field of Search ............... 424/447, 195.1; 514/423, 453, 284

[56] References Cited

U.S. PATENT DOCUMENTS

| | | | |
|---|---|---|---|
| 3,694,557 | 9/1972 | Persinos | 424/279 |
| 4,120,964 | 10/1978 | Hartenstein | 424/258 |
| 4,183,939 | 1/1980 | Gieske | 424/258 |
| 4,597,961 | 7/1986 | Etscorn | 424/448 |
| 4,782,077 | 11/1988 | de la Parra | 514/423 |
| 4,844,901 | 7/1989 | Keplinger | 424/195.1 |
| 5,069,904 | 12/1991 | Masterson | 424/401 |

OTHER PUBLICATIONS

Southan and Buckingham, *Dictionary of Alkaloids*, Chapman and Hall, London and New York, summary from pp. xxiv–xxv (1989).

*Webster's Third New International Dictionary*, Ed. P. B. Gove, Merriam-Webster Inc., Springfield, Mass., p. 1707 (1986).

Morrison and Boyd, *Organic Chemistry*, third edition, Allyn and Bacon, Inc. Boston, pp. 30-32 (1973).

Persinos Purdue et al., *South American Plants II: Taspine Isolation and Anti-Inflammatory Activity*, Journal of Pharmaceutical Sciences, vol. 68, No. 1, (Jan. 1979).

Vaisberg et al., "Taspine is the Cicatrizant Principle in Sangre de Grado Extracted from *Croton lechleri*", *Planta Medica* 55 (1989).

Lewis et al., "Introduction to the Ethnobotanical Pharmacopeia of the Amazonian Jivaro of Peru", *Medical and Poisonous Plants of the Tropics*, The Netherlands (1987).

*Primary Examiner*—Thurman K. Page
*Assistant Examiner*—D. Gabrielle Phelan
*Attorney, Agent, or Firm*—Rothwell, Figg, Ernst & Kurz

[57] ABSTRACT

A wound healing composition is a pharmaceutical dosage unit form including a wound-healing amount of an aporphinoid alkaloid such as taspine free acid, dissolved in a physiologically tolerable non-aqueous solvent such as dimethylsulfoxide.

37 Claims, 1 Drawing Sheet

FIG. 1

WOUND-HEALING COMPOSITION

BACKGROUND OF THE INVENTION

1. Field of the Invention

The present invention relates to compositions useful for the healing of wounds and the like.

2. Description of the Background Art

The indigenous population of the upper Amazon basin of South America have traditionally used plants and plant products for medicinal purposes. Knowledge gained from such traditional uses of medicinal plants has provided valuable contributions to Western medicine, including the benefits of both curare and quinine.

One material which is utilized medicinally by the Jivaro people of north-central Peru is the sap of the tree *Croton lechleri,* which is used for treating external cuts, wounds, various abrasions and the like, and internally to treat, for example, ulcers. The red sap of this species has been found to contain the alkaloid, taspine. The hydrochloride salt of taspine is reported to have anti-inflammatory activity. Persinos-Purdue et al., *Journal of Pharmaceutical Sciences* 68: 124–126 (1979).

U.S. Pat. No. 3,694,557 to Persinos points out that taspine is insoluble in a great many conventional vehicles, such as water, alcohol, alkaline solution and the like, but that acid salts of taspine are partially soluble in such vehicles. The Persinos patent also describes the anti-inflammatory effects of taspine salts.

Vaisberg et al., *Planta Medica* 55: 140–143 (1988), reported that the hydrochloride salt of taspine is responsible for the wound-healing activity of *Croton lechleri* sap. However, the levels of significance for taspine hydrochloride as a wound healer, as reported by Vaisberg et al., are low.

Other materials, such as growth hormones, have been proposed for promoting the healing of wounds. However, such materials are generally prohibitively expensive, and there is no wound healing agent recognized medically that is available commercially. There thus remains a need in the art for effective and economical medicaments which can be utilized to accelerate the healing rate of wounds.

SUMMARY OF THE INVENTION

In accordance with the present invention, a composition is provided which comprises a pharmaceutical dosage unit form including a wound-healing amount of an aporphinoid alkaloid dissolved in a physiologically tolerable, non-aqueous solvent. The invention is further directed to a wound dressing made up of a sterile bandage including an aporphinoid alkaloid, and to a method of treating a wound involving application to the wound of an aporphinoid alkaloid dissolved in a physiologically tolerable, non-aqueous solvent.

DETAILED DESCRIPTION OF THE PREFERRED EMBODIMENTS

According to one aspect of the present invention, an aporphinoid alkaloid is dissolved in a non-aqueous solvent delivery system to provide a wound-healing composition.

Aporphinoid alkaloids contain a tetracyclic ring system formed by phenol oxidative coupling of a benzylisoquinoline precursor. Included within this group are simple aporphines such as glaucine, dehydro derivatives of such simple aporphines, oxidative derivatives of such simple aporphines, aporphines with an aromatic isoquinoline ring and a carbonyl group such as liriodenine (so-called oxoaporphines), and miscellaneous aporphines. *Dictionary of Alkaloids,* Southan and Buckingham (eds.), Chapman and Hall, London and New York (1989). The aporphinoid alkaloids to which the present invention is applicable include isomers, analogs and derivatives thereof.

Aporphinoid alkaloids having an intact hetero ring include magnofluorine, corydine, corytuberine, danguyeeline, hernovine, arosinine, glaunine, glaunidine and bulbodione.

Miscellaneous aporphines in which the hetero ring is opened to give phenanthrene derivatives include taspine. Other miscellaneous aporphinoid alkaloids include thalphenine and its analogs, santiagonamine, sampangine, pentauregine, imerubrine, grandirubrine and duguenaine. Still other miscellaneous aporphines have lost a carbon from the opened hetero ring, mostly containing a 5-membered lactam ring, some even in which the nitrogen of the opened hetero ring has been oxidized to a nitro group, as in aristolochic acid-A. Aporphinoid alkaloids also include miscellaneous derivatives of benzylisoquinoline, such as rufescine.

Compositions in accordance with particularly preferred embodiments of the present invention include taspine in its free acid form. It has surprisingly been discovered that taspine free acid has much greater wound healing activity than taspine hydrochloride, stated as being responsible for the wound healing activity of *Croton lechleri* sap by Vaisberg et al., supra. However, because of the insolubility of taspine free acid in water, the outstanding efficacy of taspine free acid was not discovered until tests were performed with taspine free acid dissolved in suitable non-aqueous solvent delivery systems.

One physiologically tolerable non-aqueous solvent that works extremely well with taspine free acid is dimethylsulfoxide (DMSO). The levels of significance of healing using taspine free acid dissolved in DMSO have been up to $P=0.0001$. Furthermore, no effects have been found, either irritating and hence negative, or healing and thus positive, of DMSO alone when compared to controls.

Other non-aqueous solvent delivery systems include N,N-dimethylformamide (DMF) and tetrahydrofuran (THF).

In wound-healing compositions in accordance with the present invention, the aporphinoid alkaloid is dissolved in the solvent to a concentration of from about 0.1–10 mg/ml. In preferred embodiments, the alkaloid concentration is from about 1–5 mg/ml, more preferably about 2–3 mg/ml, most preferably about 2.5 mg/ml. Additionally, the alkaloid can be present in a form of a cream, salve or ointment at the above-noted concentrations.

In a method of treating a wound in accordance with the present invention, a pharmaceutical composition is applied to the wound, the composition containing a wound-healing amount of an aporphinoid alkaloid dissolved in a physiologically tolerable, non-aqueous solvent, as described above, which composition can be in the form of a cream, salve or ointment. In preferred embodiments, the pharmaceutical composition is applied to the wound so as to provide the wound with from about 1 $\mu g/cm^2$ to about 10 mg/cmz of the aporphinoid alkaloid. In more preferred embodiments, the composition is applied to the wound so as to provide the wound with from about 50–500 $\mu g/cm^2$, even more preferably about 200–300 $\mu g/cm^2$, most preferably about 250 $\mu g/cm^2$.

Advantageously, the inventive composition is applied to the wound site after cleansing thereof, and as soon as possible after the wounding. The inventive composition can be applied as a single dose, or three or more times a day over a period of time during healing. In preferred embodiments, the inventive composition is applied at least once a day for up to 10 or more days after wounding.

Figure 1:
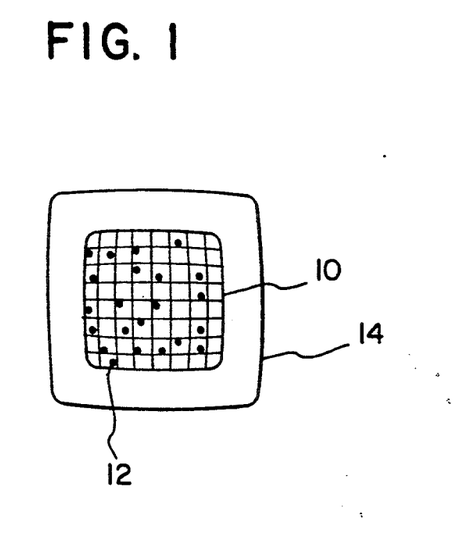
FIG. 1 is an elevational view, partly schematic, of a pre-packaged wound dressing with a sterile bandage including an aporphinoid alkaloid in accordance with the present invention.

The present invention is also applicable to a wound dressing, and preparation thereof. In accordance with this aspect of the invention, a wound dressing is provided which includes a sterile bandage 10 onto which an aporphinoid alkaloid 12 has been deposited or applied (See FIG. 1). The aporphinoid alkaloid 12 can be applied by contacting a bandage material with a solution containing the aporphinoid alkaloid and thereafter evaporating the solution from the bandage, resulting in a dried bandage containing the alkaloid. As shown in FIG. 1, the alkaloid-containing bandage can be provided sealed within a package 14.

The invention is illustrated by the following examples, which are not intended to be limiting.

EXAMPLE I

Isolation of Taspine

The viscous sap of *Croton lechleri* was mixed with four times its volume of acidic water (3.7% HCL, pH 3–4) and gently swirled in a separatory funnel with an equal amount of ethyl acetate. While rinsing the funnel with acidified water, the acidic sap mixture was drained off and the ethyl acetate discarded. This procedure was repeated three times.

To the saved acidic sap mixture, 5% NaOH solution was pipeted to achieve a pH of 9–11, and the mixture was returned to a separatory funnel with about an equal amount of ethyl acetate, rinsed and drained. This extraction was repeated three times. The basic sap mixture was discarded and the ethyl acetate solution retained. The ethyl acetate collections were combined and an equal amount of anhydrous $NaSO_4$ was added to absorb water soluble material. The ethyl acetate collection was drawn off, and the ethyl acetate was removed by rotary evaporation, leaving a whitish precipitate.

Taspine was detected using thin layer chromatography (TLC) (silica gel with fluorescent indicator $UV_{254}$) ascending in the solution chloroform/methanol 3% $NH_4OH$ in the ratio 25 ml/5 ml/0.25 ml, and observed on the TLC plates by its inhibition of the short wavelength induced influorescence of the fluophore present in the plates and by its reaction to Dragendorf's reagent (orange spot).

Once the presence of taspine was verified, the taspine mixture was dissolved in chloroform, the solute placed in a silica gel flash chromatography column, and taspine isolated using a series of gradient solutions as follows: chloroform, 10% methanol/90% chloroform, 20% methanol/80% chloroform, 20% methanol/0.01% ammonium hydroxide/79.99% chloroform, 40% methanol/0.01% ammonium hydroxide/59.99% chloroform, and 99.99% methanol/0.01% ammonium hydroxide. Each solution was poured through the column and collected in separately labeled flasks. Taspine crystallized in highest concentrations in the 20% and 40% methanol solutions as verified by TLC tests, and NMR spectral data.

EXAMPLE II

Wound Healing with Tasgine Free Acid in DMSO

Taspine free acid dissolved in DMSO to a concentration of 2.5 mg/ml was tested on rat wounds against control (DMSO alone), which in turn was tested against untreated rat wounds.

Tensile strength of the wounds 5, 7 and 12 days after administration are shown in Tables 1, 2 and 3 respectively for taspine free acid in DMSO (alkaloid +solvent) as compared to DMSO alone (solvent), and in Table 4 below for DMSO alone (solvent) as compared to no treatment.

TABLE 1

Tensile strength studies 5 days after administration.

| Rat No. | Dose Alkaloid + Solvent (newton) | Solvent-Control (newton) |
|---|---|---|
| 1 | 3.738 | 1.958 |
| 2 | 1.907 | 1.872 |
| 3 | 2.967 | 1.747 |
| 4 | 2.778 | 1.574 |
| 5 | 2.480 | 2.340 |
| 7 | 2.242 | 2.198 |
| 8 | 2.400 | 1.235 |
| 9 | 2.662 | 1.170 |
| 10 | 1.873 | 1.656 |

Alkaloid mean (X) = 2.522 ± 0.176 SEM
Solvent mean (Y) = 1.755 ± 0.118 SEM
Paired T test = 0.005
Dose: 0.25 mg alkaloid dissolved in 0.1 ml solvent
Control: 0.1 ml solvent

TABLE 2

Tensile strength studies 7 days after administration.

| Rat No. | Dose Alkaloid + Solvent (newton) | Solvent-Control (newton) |
|---|---|---|
| 1 | 3.149 | 3.059 |
| 2 | 5.016 | 3.171 |
| 3 | 4.014 | 3.237 |
| 4 | 3.865 | 2.493 |
| 5 | 3.837 | 2.469 |
| 6 | 3.526 | 2.911 |
| 7 | 3.192 | 2.747 |
| 8 | 3.306 | 2.747 |
| 9 | 3.836 | 2.714 |
| 10 | 3.878 | 2.796 |

Alkaloid mean (X) = 3.760 ± 0.17 SEM
Solvent mean (Y) = 2.810 ± 0.09 SEM
Paired T test = 0.0001
Dose: 0.25 mg alkaloid dissolved in 0.1 ml solvent
Control: 0.1 ml solvent

TABLE 3

Tensile strength studies 12 days after administration.

| Rat No. | Dose Alkaloid + Solvent (newton) | Solvent-Control (newton) |
|---|---|---|
| 1 | 5.325 | 7.778 |
| 2 | 7.314 | 5.841 |
| 3 | 5.516 | 7.638 |

TABLE 3-continued

Tensile strength studies 12 days after administration.

| Rat No. | Dose Alkaloid + Solvent (newton) | Solvent-Control (newton) |
|---|---|---|
| 4 | 8.259 | 6.412 |
| 5 | 7.018 | 7.094 |
| 6 | 5.597 | 4.982 |
| 7 | 8.440 | 9.341 |
| 8 | 7.993 | 7.056 |
| 9 | 7.050 | 9.038 |
| 10 | 9.059 | 8.375 |

Alkaloid mean (X) = 7.167 ± 0.42 SEM
Solvent mean (Y) = 7.355 ± 0.44 SEM
Paired T test = 0.72
Dose: 0.25 mg alkaloid dissolved in 0.1 ml solvent
Control: 0.1 ml solvent

TABLE 4

Tensile strength studies 7 days after administration.

| Rat No. | Dose Solvent (newton) | No Treatment-Control (newton) |
|---|---|---|
| 1 | 3.388 | 3.142 |
| 2 | 4.221 | 5.035 |
| 3 | 2.909 | 3.466 |
| 4 | 3.937 | 3.695 |
| 5 | 3.706 | 4.225 |
| 6 | 2.451 | 2.045 |
| 7 | 3.286 | 2.750 |
| 8 | 2.972 | 2.886 |
| 9 | 3.230 | 2.077 |
| 10 | 3.237 | 2.798 |

Solvent mean (X) = 3.333
Nothing mean (Y) = 3.212
Paired T test = not significant
Dose: solvent 0.1 ml
Control: nothing The above results indicate that taspine free acid in DMSO heals wounds significantly faster than DMSO alone or no treatment.

EXAMPLE III

Example II was repeated in all essential details, but utilizing an aqueous solution of taspine hydrochloride salt instead of taspine free acid in DMSO. The results of these experiments indicated that there was no significant difference between taspine hydrochloride salt solution and controls in wound healing rate.

We claim:

1. A composition comprising a pharmaceutical dosage unit form comprising an effective amount of an aporphines alkaloid sufficient to provide wound-healing, said alkaloid dissolved in a non-aqueous solvent selected from the group consisting of dimethylsulfoxide, N, N-dimethylformamide or tetrahydrofuran.

2. The composition of claim 1 wherein said alkaloid is dissolved in said solvent at a concentration of from about 0.1-10 mg/ml.

3. The composition of claim 2 wherein said concentration is about 1-5 mg/ml.

4. The composition of claim 2 wherein said concentration is about 2-3 mg/ml.

5. The composition of claim 2 wherein said concentration is about 2.5 mg/ml.

6. The composition of claim 1 wherein said alkaloid is selected from the group consisting of taspine, thalphenine, santiagonamine, sampangine, pentaureqine, imerubrine, grandirubrine, duguenaine, magnofluorine, hernovine, glaunine, glaunidine, arosinine, bulbodione, glaucine, liriodenine, aristolochic acid-A, and rubescine.

7. The composition of claim 1 wherein said alkaloid is selected from the group consisting of taspine, thalphenine, santiagonamine, sampangine, pentauregine, imerubrine, grandirubrine, and duguenaine.

8. The composition of claim 1 wherein said alkaloid is taspine free acid.

9. A composition comprising comprising an effective amount of taspine free acid sufficient to provide wound-healing, said, taspine free acid dissolved in a solvent selected from the group consisting of dimethylsulfoxide, N,N-dimethylformamide or tetrahydrofuran.

10. The composition of claim 9 wherein said solvent is dimethylsulfoxide.

11. A composition comprising a pharmaceutical dosage unit form comprising an effective amount of taspine free acid sufficient to provide wound-healing, said taspine free acid dissolved in a non-aqueous solvent "selected from the group consisting of dimethylsulfoxide, N, N-dimethylformamide or tetrahydrofuran".

12. A wound dressing comprising a sterile bandage including an effective amount of an aporphine alkaloid sufficient to provide wound-healing.

13. The wound dressing of claim 12 wherein said alkaloid is selected from the group consisting of taspine, thalphenine, santiagonamine, sampangine, pentauregine, imerubrine, grandirubrine, duguenaine, magnofluorine, hernovine, glaunine, glaunidine, arosinine, bulbodione, glaucine, liriodenine, aristolochic acid-A and rubescine.

14. The wound dressing of claim 12 wherein said alkaloid is selected from the group consisting of taspine, thalphenine, santiagonamine, sampangine, pentauregine, imerubrine, grandirubrine, and duguenaine.

15. The wound dressing of claim 12 wherein said alkaloid is taspine.

16. The wound dressing of claim 12 wherein said alkaloid is taspine free acid.

17. A pre-packaged wound dressing comprising a sterile bandage including an effective amount of an aporphinoid alkaloid sufficient to provide wound healing, which bandage is sealed within a package.

18. The wound dressing of claim 17 wherein said alkaloid is selected from the group consisting of taspine, thalphenine, santiagonamine, sampangine, pentauregine, imerubrine, grandirubrine, duguenaine, magnofluorine, hernovine, glaunine, glaunidine, arosinine, bulbodione, glaucine, liriodenine, aristolochic acid-A, and rubescine.

19. The wound dressing of claim 17 wherein said alkaloid is selected from the group consisting of taspine, thalphenine, santiagonamine, sampangine, pentauregine, imerubrine, grandirubrine, and duguenaine.

20. The wound dressing of claim 17 wherein said alkaloid is taspine.

21. The wound dressing of claim 17 wherein said alkaloid is taspine free acid.

22. A method of preparing a wound dressing comprising:
   a) providing a bandage;
   b) providing a non-aqueous solution of an effective amount of an aporphinoid alkaloid "sufficient to provide wound-healing, said non-aqueous solution selected from the group consisting of dimethylsulfoxide, N, N-dimethylformamide or tetrahydrofuran;"
   c) contacting the bandage with said solution; and d) evaporating said solution so as to apply said alkaloid to said bandage.

23. The method of claim 22 wherein said solution is provided as a solution containing an alkaloid selected from the group consisting of taspine, thalphenine, santiagonamine, sampangine, pentauregine, imerubrine, grandirubrine, duguenaine, magnofluorine, hernovine, glaunine, glaunidine, arosinine, bulbodione, glaucine, liriodenine, aristolochic acid-A, and rubescine.

24. The method of claim 22 wherein said solution is provided as a solution containing an alkaloid selected from the group consisting of taspine, thalphenine, santiagonamine, sampangine, pentauregine, imerubrine, grandirubrine, and duguenaine.

25. The method of claim 22 wherein said solution is provided as a solution containing an taspine.

26. The method of claim 25 wherein said solution is provided as a solution containing taspine free acid.

27. A method of treating a wound comprising applying to said wound a pharmaceutical composition including an effective amount of an aporphine alkaloid sufficient to provide wound-healing dissolved in a physiologically tolerable, non-aqueous solvent "selected from the group consisting of dimethylsulfoxide, N, N-dimethylformamide or tetrahydrofuran."

28. The method of claim 27 wherein said composition is applied in a pharmaceutical dosage unit form containing an aporphine alkaloid selected from the group consisting of taspine, thalphenine, santiagonamine, sampangine, pentauregine, imerubrine, grandirubrine, duguenaine, magnofluorine, hernovine, glaunine, glaunidine, arosinine, bulbodione, glaucine, liriodenine, aristolochic acid-A, and rubescine.

29. The method of claim 27 wherein said composition is applied as a pharmaceutical dosage unit including an aporphine alkaloid selected from the group consisting of taspine, thalphenine, santiagonamine, sampangine, pentauregine, imerubrine, grandirubrine, and duguenaine.

30. The method of claim 27 wherein said composition is applied as a pharmaceutical dosage unit form comprising taspine free acid in a non-aqueous solvent selected from the group consisting of dimethylsulfoxide, N,N-dimethylformamide or tetrahydrofuran.

31. The method of claim 30 wherein said composition is applied as a dimethylsulfoxide solution of taspine free acid.

32. The method of claim 27 wherein said composition is applied to said wound so as to provide said wound with from about 1 $\mu g/cm^2$ to about 10 $mg/cm^2$ of said alkaloid.

33. The method of claim 27 wherein said composition is applied to said wound so as to provide said wound with about 50–500 $\mu g/cm^2$ of said alkaloid.

34. The method of claim 33 wherein a dimethylsulfoxide solution of taspine free acid is applied to said wound.

35. The method of claim 34 wherein said composition is applied to said wound so as to provide said wound with about 200–300 $\mu g/cm^2$ of taspine free acid.

36. The method of claim 34 wherein said composition is applied to said wound so as to provide said wound with about 250 $\mu g/cm^2$ of taspine free acid.

37. The composition of claim 2 in the form of a cream, salve or ointment.

* * * * *

UNITED STATES PATENT AND TRADEMARK OFFICE
CERTIFICATE OF CORRECTION

PATENT NO. : 5,156,847
DATED : October 20, 1992
INVENTOR(S) : Walter H. Lewis et al.

It is certified that error appears in the above-identified patent and that said Letters Patent is hereby corrected as shown below:

Column 6, claim 9, line 1, delete second occurrence of "comprising".

Column 6, claim 11, line 4, delete """ (the quotation mark before "se-") and line 6, delete """ (the quotation mark after "tetrahydrofuran").

Signed and Sealed this

Ninth Day of November, 1993

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,156,847　　　　　　　　　　　　　　Page 1 of 2

DATED : October 20, 1992

INVENTOR(S) : Walter H. Lewis et al.

It is certified that error appears in the above-identified patent and that said Letters Patent is hereby corrected as shown below:

Col. 3, lines 5, 8, 9 and 10, "µg" should be --ug--.

Col. 3, line 5, "cmz" should be --cm$^2$--.

Col. 4, line 10, "Tasgine" should be --Taspine--.

Col. 5, line 51 (claim 1), "aporphines" should be --aporphine--.

Col. 5, line 66 (claim 6), "pentaureqine" should be --pentauregine--.

Col. 6, line 11 (claim 9), "said," should be --said--.

Col. 6, line 63 (claim 22), " "sufficient" should be -- sufficient--.

Col. 6, line 67 (claim 22), "ran;" " should be --ran; --.

UNITED STATES PATENT AND TRADEMARK OFFICE
CERTIFICATE OF CORRECTION

PATENT NO. : 5,156,847

DATED : October 20, 1992

INVENTOR(S) : Walter H. Lewis et al.

It is certified that error appears in the above-identified patent and that said Letters Patent is hereby corrected as shown below:

Col. 7, line 23 (claim 27), " "selected" should be -- selected--.

Col. 7, line 25 (claim 27), "tetrahydrofuran." " should be --tetrahydrofuran. --.

Col. 8, line 17 (claim 32), "µg" should be --ug--.

Col. 8, line 21 (claim 33), "µg" should be --ug--.

Col. 8, line 27 (claim 35), "µg" should be --ug--.

Col. 8, line 30 (claim 36), "µg" should be --ug--.

Signed and Sealed this

Seventh Day of December, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,156,847
DATED : October 20, 1992
INVENTOR(S) : Walter H. Lewis et al.          Page 1 of 2

It is certified that error appears in the above-identified patent and that said Letters Patent is hereby corrected as shown below:

Title Page:

In the Abstract, line 3, before "acid" insert --of--.

Col. 2,   line 35, before "acid" insert --of--.
Col. 2,   line 39, before "acid" insert --of--.
Col. 2,   line 40, before "acid" insert --of--.
Col. 2,   line 42, before "acid" insert --of--.
Col. 2,   line 45, before "acid" insert --of--.
Col. 2,   line 47, before "acid" insert --of--.
Col. 4,   line 10, before "acid" insert --of--.
Col. 4,   line 12, before "acid" insert --of--.
Col. 4,   line 18, before "acid" insert --of--.
Col. 6,   line 8,  before "acid" insert --of--.
Col. 6,   line 10, before "acid" insert --of--.
Col. 6,   line 11, before "acid" insert --of--.
Col. 6,   line 18, before "acid" insert --of--.

UNITED STATES PATENT AND TRADEMARK OFFICE
CERTIFICATE OF CORRECTION

PATENT NO. : 5,156,847
DATED : October 20, 1992
INVENTOR(S) : Walter H. Lewis et al.

It is certified that error appears in the above-identified patent and that said Letters Patent is hereby corrected as shown below:

Col. 6, line 19, before "acid" insert --of--.

Col. 6, line 39, before "acid" insert --of--.

Col. 6, line 58, before "acid" insert --of--.

Col. 7, line 18, before "acid" insert --of--.

Col. 8, line 9, before "acid" insert --of--.

Col. 8, line 14, before "acid" insert --of--.

Col. 8, line 23, before "acid" insert --of--.

Col. 8, line 27, before "acid" insert --of--.

Col. 8, line 30, before "acid" insert --of--.

Signed and Sealed this

Twenty-sixth Day of April, 1994

*Attest:*

BRUCE LEHMAN

*Attesting Officer*     *Commissioner of Patents and Trademarks*